United States Patent [19]

Beitzke et al.

[11] Patent Number: 4,668,788

[45] Date of Patent: May 26, 1987

[54] 5,5-DICHLORO-4,5-DIHYDRO-6-HYDROXY-2-TRICHLOROMETHYLPYRIMIDIN-4-ONE

[75] Inventors: Bernhard Beitzke, Bergisch Gladbach; Heinz U. Blank, Odenthal, both of Fed. Rep. of Germany

[73] Assignee: Bayer Aktiengesellschaft, Leverkusen, Fed. Rep. of Germany

[21] Appl. No.: 766,586

[22] Filed: Aug. 19, 1985

[30] Foreign Application Priority Data

Aug. 29, 1984 [DE] Fed. Rep. of Germany ....... 3431698

[51] Int. Cl.$^4$ ............................................. C07D 239/22
[52] U.S. Cl. ..................................... 544/319; 544/334
[58] Field of Search ........................................ 544/319

[56] References Cited

U.S. PATENT DOCUMENTS 4,413,999 11/1983 Linder et al. ...................... 544/319

Primary Examiner—John M. Ford
Attorney, Agent, or Firm—Connolly & Hutz

[57] ABSTRACT

The new compound 5,5-dichloro-4,5-dihydro-6-hydroxy-2-trichloromethylpyrimidin-4-one can be prepared by reacting 4,6-dihydroxy-2-methylpyrimidine or chlorinated subsequent stages with a chlorinating agent. 5,5-dichloro-4,5-dihydro-6-hydroxy-2-trichloromethylpyrimidin-4-one can be used as an intermediate for the preparation of 2-trichloromethyl-4,5,6-trichloropyrimidine.

1 Claim, No Drawings

5,5-DICHLORO-4,5-DIHYDRO-6-HYDROXY-2-TRICHLOROMETHYLPYRIMIDIN-4-ONE

The invention relates to 5,5-dichloro-4,5-dihydro-6-hydroxy-2-trichloromethylprimidin-4-one, a process for its preparation and its use for the preparation of 2-trichloromethyl-4,5,6-trichloropyrimidine.

2-Trichloromethyl-4,5,6-trichloropyrimidine of the formula

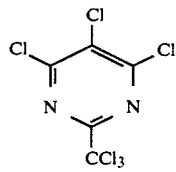

can be prepared from 2-cyanoethylamines by chlorination (C.A. 74, 100079d). 2-Trichloromethyl-4,5,6-trichloropyrimidine is obtained in maximum yields of only 60% by this process. Undesirable by-products, such as, for example, hexachloroethane, are also formed here.

The new compound 5,5-dichloro-4,5-dihydro-6-hydroxy-2-trichloromethylpyrimidin-4-one has been found.

5,5-Dichloro-4,5-dihydro-6-hydroxy-2-trichloromethylpyrimidin-4-one can be described by the formula

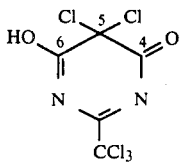

The 5,5-dichloro-4,5-dihydro-6-hydroxy-2-trichloromethylpyrimidin-4-one according to the invention can of course also exist in one of its tautomeric forms.

The new compound is an intermediate for the preparation of 2-trichloromethyl-4,5,6-trichloropyrimidine. 2-Trichloromethyl-4,5,6-trichloropyrimidine can be prepared in high yields and without undesirable by-products via the intermediate.

A process has also been found for the preparation of 5,5-dichloro-4,5-dihydro-6-hydroxy-2-trichloromethylpyrimidin-4-one, which is characterised in that 4,6-dihydroxy-2-methylpyrimidine or chlorinated subsequent stages is or are reacted with a chlorinating agent.

4,6-Dihydroxy-2-methylpyrimidine of the formula

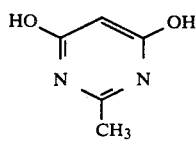

is known per se (J. Org. Chem. 17, 1320 to 1321 (1952)). It can be prepared, for example, by reacting acetamidine with diethyl malonate in the presence of sodium ethylate.

Chlorinated subsequent stages of 4,6-dihydroxy2-methylpyrimidine are those with 1 to 4 chlorine atoms. An example which may be mentioned here is the known compound 5-chloro-4,6-dihydroxy-2-methylpyrimidine of the formula

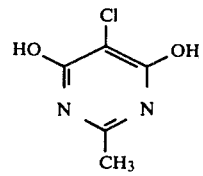

(J. Org. Chem. 26, 1874 to 1877 (1961)). Preferred starting substances for the preparation of the 5,5-di- chloro-4,5-dihydro-6-hydroxy-2-trichloromethylpyrimidin-4-one according to the invention are 4,6-dihydroxy-2methylpyrimidine and 5-chloro-4,6-dihydroxy-2-methylpyrimidine. 4,6-Dihydroxy-2-methylpyrimidine is particularly preferred.

Examples of chlorinating agents for the process according to the invention are elemental chlorine, sulphuryl chloride, chloro-amines or chloro-amides, such as N-chlorosuccinimide, a mixture of hydrogen chloride and hydrogen peroxide, iodine chloride, bromine chloride and acid chlorides, such as phosphorus pentachloride. Preferred chlorinating agents are elemental chlorine and sulphuryl chloride. Chlorine is particularly preferred.

The chlorinating agent is preferably employed in at least the stoichiometric amount, based on the 4,6-dihydroxy-2-methylpyrimidine employed or the chlorinated subsequent stages. In general, 5 to 7 moles, preferably 5.1 to 6 moles, of the chlorinating agent, based on the 4,6-dihydroxy-2-methylpyrimidine are employed.

The chlorination according to the invention can be carried out in the presence of catalysts. Examples of catalysts which may be mentioned are:

Amines (for example primary, secondary and tertiary aliphatic amines, such as triethylamine, N,N-diisopropyl-N-ethylamine, 1,8-bis-(dimethyl-amino)-naphthalene, 1,4diazabicyclo[2,2,2]octane (DABCO), N-methylpiperidine and N-methylpyrrolidine, heterocyclic amines, such as, for example, pyridine, lutidine, collidine, quinoline, acridine, 4-dimethylaminopyridine, imidazole and N-methylimidazole, amidines, such as formamidine, 1,5-diazabicyclo[4,3,0]non-5-ene (DBN) and 1,8-diazabicyclo[5,4,0]- undec-7-ene (DBU)), Phosphorus compounds (such as triphenylphosphine, triphenylphosphine oxide, phosphorus trichloride and phosphorus pentachloride), Carboxylic acid amides (such as dimethylformamide, dimethylacetamide and N-methylpyrrolidone, phthalimide and succinimide), Nitriles (such as acetonitrile and benzonitrile), Friedel-Crafts catalysts (such as aluminium chloride, iron trichloride, gallium trichloride, zinc chloride, copper dichloride, tin tetrachloride and titanium tetrachloride), Iodine or sulphur, and Agents which form free radicals (peroxides, such as, for example, dibenzoyl peroxide, and azo compounds, such as, for example, azo-bis-(isobutyronitrile)).

Preferred catalysts are: triethylamine, phosphorus trichloride, iron(III) chloride, dimethylformamide, iodine and benzoyl peroxide.

The catalyst is in general employed in an amount of 0.01 to 5 mol %, preferably 0.1 to 3 mol %, based on the starting compound.

The process according to the invention is preferably carried out in the presence of a solvent or suspending agent. Solvents or suspending agents for the process according to the invention are compounds which are liquid under the reaction conditions and inert towards chlorine and do not react with the starting compounds under the reaction conditions. Examples which may be mentioned are chlorinated hydrocarbons, such as chlorobenzene, the isomeric dichlorobenzenes, the isomeric trichlorobenzenes, carbon tetrachloride, chloroform and hexachloroethane, fluorochlorohydrocarbons, such as 1,1,2-trichloro-1,2,2trifluoroethane, benzene, phosphorus trichloride and phosphorus oxychloride. Preferred solvents or suspending agents are the chlorinated benzenes and phosphorus oxychloride.

The chlorination can lead either to a suspension or to a solution of the 5,5-dichloro-4,5-dihydro-6-hydroxy-2-trichloromethylpyrimidin-4-one. The concentration of the educt can be chosen so that a solution or a suspension is present at the end of the chlorination. The concentrations of the educt are preferably between 0.5 and 8 moles/l of solvent or suspending agent.

The chlorination can also be carried out under irradiation with light. Light with a wavelength of 240 to 750 nm, preferably 320 to 500 nm, is in general used.

The chlorination according to the invention is in general carried out in the temperature range from 20° to 180° C., preferably from 30° to 160° C. and particularly preferably from 30° to 120° C.

In phosphorus oxychloride as the solvent or suspending agent, it is advantageous to carry out the chlorination between 30° and 70° C. so that no reaction yet takes place on the oxo groups in the 4- and/or 6-position.

In the chlorinated benzenes, the chlorination is preferably carried out between 60° and 160° C.

The process according to the invention is in general carried out under normal pressure. However, it is also possible to carry out the chlorination under reduced or increased pressure (for example in the pressure range from 0.1 to 10 bar).

The 5,5-dichloro-4,5-dihydro-6-hydroxy-2-trichloromethylpyrimidine-4-one according to the invention can be used for the preparation of 2-trichloromethyl-4,5,6 -trichloropyrimidine. The preparation of 2-trichloromethyl-4,5,6-trichloropyrimidine is characterised in that 5,5-dichloro-4,5-dihydro-6-hydroxy-2-trichloromethylpyrimidin-4-one is reacted with an acid chloride, if appropriate in the presence of a halogen of the formula XCl wherein X denotes chlorine, bromine or iodine, and if appropriate in the presence of a catalyst.

Acid chlorides are in general phosphorus oxychloride, thionyl chloride, phosgene, oxalyl chloride, phosphorus trichloride, phosphorus pentachloride, dichlorophosphoranes, sulphur dichloride and disulphur dichloride.

Preferred acid chlorides are phosgene, phosphorus oxychloride and/or phosphorus pentachloride or phosphorus trichloride and chlorine.

Phosphorus oxychloride and/or phosphorus pentachloride or phosphorus trichloride and chlorine are particularly preferably used.

The acid chloride is in general employed in an amount of 2 to 3 moles, preferably 2 to 2.5 moles, per mole of 5,5-dichloro-4,5-dihydro-6-hydroxy-2-trichloromethylpyrimidin-4-one.

If appropriate, the reaction can be carried out in the presence of a halogen. Halogens which may be mentioned are chlorine, bromine chloride or iodine chloride, preferably chlorine.

The halogens are in general employed in an amount of 0 to 3 moles, preferably 0 to 2 moles, per mole of 5,5-dichloro-4,5-dihydro-6-hydroxy- 2-trichloromethylpyrimidin-4-one.

The preparation of 2-trichloromethyl-4,5,6-trichloropyrimidine is in general carried out in the temperature range from 40° to 200° C., preferably from 50° to 180° C. and particularly preferably from 60° to 140° C.

The preparation of 2-trichloromethyl-4,5,6-trichloropyrimidine is in general carried out under normal pressure. However, it is also possible to carry out the reaction under reduced or increased pressure (for example in the pressure range from 0.1 to 10 bar).

If appropriate, the process according to the invention can be carried out in the presence of a catalyst. As a rule, the same catalysts which can be employed in the chlorination can be used.

The preparation of 2-trichloromethyl-4,5,6-trichloropyrimidine is preferably carried out in a solvent or suspending agent. Solvents or suspending agents which can be used are as a rule the same as those which can b e employed in the chlorination.

The preparation of 5,5-dichloro-4,5-dihydro-6-hydroxy-2-trichloromethylpyrimidin-4-one and 2-trichloromethyl-4,5,6-trichloropyrimidine can be carried out, for example, as follows:

The 4,6-dihydroxy-2-methylpyrimidine is taken, if appropriate in a solvent or suspending agent and if appropriate in the presence of the catalyst, and the chlorinating agent is metered in. It is of course also possible for the 4,6-dihydroxy-2-methylpyrimidine and the chlorinating agent to be metered simultaneously into a solvent or suspending agent. After the reaction, the 5,5-dichloro-4,5-dihydro-6-hydroxy-2-trichloromethyl-pyrimidin-4-one is isolated by filtration with suction and can then be further reacted to give 2-trichloromethyl-4,5,6-trichloropyrimidine.

For this reaction, the 5,5-dichloro-4,5-dihydro-6-hydroxy-2-trichloromethylpyrimidin-4-one is taken in a solvent or suspending agent and the acid chloride is added. The mixture is allowed to react until the evolution of gas has ended.

In a preferred embodiment of the process according to the invention, the preparation of the 2-trichloromethyl-4,5,6-trichloropyrimidine from the 4,6-dihydroxy-2-methylpyrimidine or a chlorinated subsequent stage is carried out in a one-pot reaction, without isolation of the 5,5-dichloro-4,5-dihydro-6-hydroxy-2-trichloromethyl- pyrimidine-4-one. In this preferred embodiment, the acid 30. chloride is added to the reaction mixture of the first stage.

However, it is also possible to react 4,6 -dihydroxy-2-methylpyrimidine or one of its chlorinated subsequent stages with less than the stoichiometric amount (for example at leaat 1 mole, based on the starting compound) of chlorine or compound which splits off chlorine in the first stage and to react the resultin g reaction mixture with an acid chloride and the required residual amount of chlorine or compound which splits off chlorine in the second stage.

In a particularly preferred embodiment, some of the phosphorus trichloride is added to the reaction mixture from the first stage, which can already contain the catalyst, after which the remainder of the phosphorus trichloride and the total amount of chlorine still required are passed in simultaneously. When the metering has ended, the mixture is heated until the evolution of gas has ended.

The 2-trichloromethyl-4,5,6-trichloropyrimidine is in general isolated by distillation.

2-Trichloromethyl-4,5,6-trichloropyrimidine is an intermediate for dyestuffs (German Offenlegungsschrift No. 2,325,602 and German Offenlegungsschrift No. 2,326,112). It can also be used as an intermediate for herbicides and fungicides and for pyrimidyl isocyanates (U.S. Pat. Specification 3,772,313).

EXAMPLE 1

5,5-Dichloro-4,5-dihydro-6-hydroxy-2-trichloromethyl-pyrimidin-4-one 210 g of chlorine were passed into a suspension of 63.1 g (0.5 mole) of 4,6-dihydroxy-2-methylpyrimidine in 500 ml of o-dichlorobenzene at 120° to 125° C. After the chlorine had been passed in for 5 to 6 hours, the components had formed a solution. The solution was subsequently stirred at 125° C. for a further hour and was allowed to cool and left to stand for 12 hours, and the crystals precipitated were then filtered off with suction at 20° C. and rinsed with a little petroleum benzine. Yield: 132 g (0.442 mole), 89% of theory.

A portion of the product was sublimed at a bath temperature of 150° C. under 0.01 mm Hg. Colourless crystals of melting point 150 to 160oC were obtained.

$C_5HCl_5N_2O_2$ (298.34):

Calculated: C 20.13; H 0.34; N 9.40; Cl 59.40:
Found: C 19.9; H 0.7; N 9.4; Cl 59.40:

Mass spectrum: m/e=296 (M+), base peak m/e=110 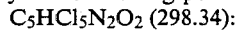 ($Cl_2CCO$)

EXAMPLE 2

2-Trichloromethyl-4,5,6-trichloropyrimidine 63.1 g (0.5 mole) of 4,6-dihydroxy-2-methylpyrimidine in 500 ml of o-dichlorobenzene were taken in a 1 liter four-necked flask with a stirrer, thermometer, gas inlet tube and reflux condenser with bubble counter. 238 g of chlorine were passed in at a bottom temperature of 130° C. in the course of 5 hours, after which the components had formed a solution.

The solution was stirred at 130° C. for a further hour.

Thereafter, 13.8 g (0.1 mole) of $PCl_3$ and 1.5 g of triethylamine were added at 20° C. 123.6 g (0.9 mole) of $PCl_3$ and 35.5 g (0.5 mole) of chlorine were then simultaneously metered in, starting at 60° C., up to 115° C. After the metering in, the mixture was subsequently stirred at 120° C. for a further 2 hours, until the evolution of gas had ended.

After the phosphorus oxychloride and o-dichlorobenzene had been distilled off, 130.1 g of 2-trichloromethyl-4,5,6 -trichloropyrimidine were distilled over at an overhead temperature of 140° C. under 2.5 mbar. This corresponds to a yield of 87% of theory. Melting point: 63 to 64° C.

EXAMPLE 3

126.1 g (1 mole) of 4,6-dihydroxy-2-methylpyrimidine in 500 ml of o-dichlorobenzene were taken in a 1 four-necked flask with a stirrer, thermometer, gas inlet tube and reflux condenser with bubble counter and were heated up to 120° C. 420 g of chlorine were passed in at 120°-130° C. in the course of 6 hours, after which the components had formed a solution. The solution was subsequently stirred at 120° C. for a further hour. 3 g of triethylamine and 27.6 g (0.2 mole) of phosphorus trichloride were then added and 247.2 g (1.8 moles) of phosphorus trichloride and 71 g of chlorine were metered in simultaneously at 110°-120° C. in the course of about 45 minutes. The mixture was subsequently stirred at 120° C. for a further 2 hours, until the evolution of gas had ended, and was then worked up by distillation. After the phosphorus oxychloride and o-dichlorobenzene had been distilled off, 264.7 g (88%) of 2-trichloromethyl-4,5,6trichloropyrimidine were obtained.

EXAMPLE 4

2-Trichloromethyl-4,5,6-trichloropyrimidine 149.2 g (0.5 mole) of 5,5-dichloro-4,5-dihydro-6-hydroxy-2-trichloromethylpyrimidin-4-one in 230 g of phosphorus oxychloride were taken in a 500 ml four-necked flask with a stirrer, thermometer, gas inlet tube, dropping funnel and reflux condenser with bubble counter and were warmed to 60° C., during which gentle evolution of gas was observed. After 1.5 g of triethylamine had been added, 137.4 g (1 mole) of phosphorus trichloride and 35.5 g (0.5 mole) of $Cl_2$ were simultaneously metered in over a period of 1 hour, during which the mixture was warmed to 115° C. The mixture was subsequently stirred at 120° C. for a further 2 hours, until the evolution of gas had ended. After the phosphorus oxychloride (about 370 g) had been distilled off, 142.8 g of 2-trichloromethyl-4,5,6-trichloropyrimidine, corresponding to a yield of 95% of theory, were distilled over at an overhead temperature of 140° C. under 2.5 mbar.

EXAMPLE 5

416 g of phosphorus oxychloride were taken in a 500 ml four-necked flask with a solids metering machine, gas inlet tube, mechanical stirrer, dropping funnel, thermometer, reflux condenser and bubble counter and were warmed to 50° C. and saturated with chlorine gas. 63.1 g of 4,6-dihydroxy-2-methylpyrimidine, via the solids metering machine, and 207 g of chlorine were then simultaneously introduced at 50° C. in the course of 170 minutes. Thereafter, the mixture was stirred at 80° C. for a further 1.5 hours and 1.5 g of triethylamine and 13.7 g of phosphorus trichloride were added dropwise. After the mixture had been heated to the reflux temperature (103° C.), 123.7 g of phosphorus trichloride and 35.8 g of chlorine were simultaneously metered in over a period of 1 hour. After dropwise addition of the $PCl_3$, 35.2 g of chlorine were subsequently metered in over a period of 18 minutes. The mixture was stirred under reflux for a further 75 minutes, until the evolution of gas had ended, and was then worked up by distillation. 539.2 g of phosphorus oxychloride and 147.7 g of 98.5% pure 4,5,6-trichloro-2trichloromethylpyrimidine (96.7% of theory) were obtained.

EXAMPLE 6

103 g of phosphorus oxychloride were taken in an apparatus as in Example 5 and were warmed to 50° C. and saturated with chlorine. 63.1 g of 4,6-dihydroxy-2-methylpyrimidine and 183 g of chlorine were introduced simultaneously in the course of 143 minutes. Thereafter, the suspension was warmed to 65° C. and further chlorine was passed in, after which the components had formed a yellow paste. The temperature was increased to 75°–80° C., after which an easily stirrable suspension was obtained. A total of 54.5 g of chlorine were subsequently metered in during the heating-up. The mixture was allowed to react at 80° C. for a further 20 minutes and 1.5 g of triethylamine were then added. 13.7 g of phosphorus trichloride were then added dropwise in the course of 7 minutes and the suspension was heated to 106° C., after which 123.7 g of phosphorus trichloride and 35.6 g of chlorine were simultaneously metered in. Thereafter, 23.4 g of chlorine were subsequently metered in for a further 34 minutes, until the mixture was saturated with chlorine. The mixture was stirred under reflux for a further 17 minutes and then distilled. 217 g of phosphorus oxychloride and 143.6 g of 95.9% 4,5,6-trichloro-2-trichloromethylpyrimidine (91.6% of theory) were obtained.

EXAMPLE 7

100 ml of o-dichlorobenzene and 2.8 g of triphenylphosphine oxide were taken in a 1 l four-necked flask with a stirrer, thermometer, Claisen attachment, dry ice condenser with bubble counter, inlet tube and heatable dropping funnel. 115 g of phosgene and a solution, warmed to 100° C., of 5,5-dichloro-4,5-dihydro-6-hydroxy-2-trichloromethylpyrimidin-4-one, which had been prepared by chlorination of 63.1 g (0.5 mole) of 4,6-dihydroxy-2-methylpyrimidine with 238 g of chlorine at 100° C., in 500 ml of ortho-dichlorobenzene were then simultaneously metered in at a bottom temperature of 150° C. in the course of 7 hours.

After the metering in, the mixture was stirred under reflux for a further hour and the excess phosgene was then stripped off under 20 mbar.

After the o-dichlorobenzene had been distille d off and the product had been distilled over a Vigreux column, 126.3 g of 92% pure 4,5,6-trichloro-2-trichloromethylpyrimidine (77.3% of theory, based on the 4,6-dihydroxy-2-methylpyrimidine) were obtained.

We claim:
1. 5,5-Dichloro-4,5-dihydro-6-hydroxy-2-trichloromethylpyrimidin-4-one.

* * * * *